(12) United States Patent
Wainman et al.

(10) Patent No.: US 9,605,235 B2
(45) Date of Patent: Mar. 28, 2017

(54) SOFTENING COMPOSITIONS INCLUDING FERMENTED FRUIT SOLUTIONS AND METHODS FOR MAKING AND USING THE SAME

(71) Applicant: EQUATOR GLOBAL LIMITED, Tortola (VG)

(72) Inventors: Peter Nelson Wainman, Bangkok (TH); Sirilak Narongtanupone, Bangkok (TH); Rosalin Dokphut, Ubon Ratchathani (TH); Areerat Lertamornchaikul, Bangkok (TH); Sungworn Sangsri

(73) Assignee: EQUATOR GLOBAL LIMITED, Road Town, Tortola (VG)

( * ) Notice: Subject to any disclaimer, the term of this patent is extended or adjusted under 35 U.S.C. 154(b) by 0 days.

(21) Appl. No.: 15/248,919

(22) Filed: Aug. 26, 2016

(65) Prior Publication Data

US 2016/0362639 A1    Dec. 15, 2016

Related U.S. Application Data

(63) Continuation of application No. 14/768,715, filed as application No. PCT/IB2014/061567 on May 20, 2014, now Pat. No. 9,434,912.

(30) Foreign Application Priority Data

Sep. 20, 2013  (WO) .................. PCT/IB2013/002069

(51) Int. Cl.

| | | |
|---|---|---|
| C11D 3/382 | (2006.01) |
| C11D 3/43 | (2006.01) |
| C11D 7/44 | (2006.01) |
| C11D 7/50 | (2006.01) |
| C11D 3/38 | (2006.01) |
| C11D 1/12 | (2006.01) |
| C11D 1/66 | (2006.01) |
| C11D 3/00 | (2006.01) |
| C11D 3/04 | (2006.01) |
| C11D 3/20 | (2006.01) |
| C11D 3/22 | (2006.01) |
| C12P 1/04 | (2006.01) |

(52) U.S. Cl.
CPC .................. *C11D 3/38* (2013.01); *C11D 1/12* (2013.01); *C11D 1/662* (2013.01); *C11D 3/001* (2013.01); *C11D 3/0047* (2013.01); *C11D 3/0073* (2013.01); *C11D 3/0084* (2013.01); *C11D 3/042* (2013.01); *C11D 3/046* (2013.01); *C11D 3/2048* (2013.01); *C11D 3/2079* (2013.01); *C11D 3/221* (2013.01); *C11D 3/382* (2013.01); *C12P 1/04* (2013.01)

(58) Field of Classification Search
CPC .. C11D 3/382; C11D 3/43; C11D 7/44; C11D 7/50; C11D 11/0017; C11D 9/265; C11D 3/042

See application file for complete search history.

(56) References Cited

U.S. PATENT DOCUMENTS

| | | |
|---|---|---|
| 6,653,272 B1 | 11/2003 | Uyama |
| 7,083,727 B2 | 8/2006 | Tanaka et al. |
| 7,538,079 B2 | 5/2009 | Warr et al. |
| 8,440,598 B2 | 5/2013 | Sehgal et al. |
| 8,778,860 B2 | 7/2014 | Saint Victor |
| 2006/0240147 A1 | 10/2006 | Padhye |
| 2010/0144584 A1 | 6/2010 | Saint Victor |
| 2010/0233128 A1 | 9/2010 | Panasenko |
| 2010/0316752 A1 | 12/2010 | Hsu |
| 2011/0142990 A1 | 6/2011 | Jacob |
| 2011/0311680 A1 | 12/2011 | Takase et al. |
| 2012/0246854 A1 | 10/2012 | Uchiyama et al. |

FOREIGN PATENT DOCUMENTS

| | | |
|---|---|---|
| CN | 101077999 A | 11/2007 |
| CN | 101126052 A | 2/2008 |
| CN | 102015994 A | 4/2011 |
| CN | 102071113 A | 5/2011 |
| CN | 102655740 A | 9/2012 |
| CN | 102888427 A | 1/2013 |
| EP | 1178108 A1 | 2/2002 |
| JP | 6219082 A | 1/1987 |
| JP | 2001152188 A | 6/2001 |
| JP | 2002003886 A | 1/2002 |
| JP | 2006341236 A | 12/2006 |
| JP | 2010194532 A | 9/2010 |
| TW | 490485 B | 6/2002 |

(Continued)

OTHER PUBLICATIONS

Notification of Transmittal of the International Search Report and Written Opinion dated Mar. 18, 2014, in International Application No. PCT/IB2013/02069, 10 pages.
Notification of Transmittal of the International Search Report and Written Opinion dated Dec. 19, 2014, in International Application No. PCT/IB2014/061567, 7 pages.
Notification of Transmittal of the International Search Report and Written Opinion dated Mar. 18, 2014, in International Application No. PCT/IB2013/02180, 9 pages.
Notification of Transmittal of the International Search Report and Written Opinion dated Jul. 30, 2014, in International Application No. PCT/IB2013/02320, 12 pages.
Nutrimax Organic "How to Make & Use Garbage Enzyme", 2010, 5 pages.
Sossou et al. "Study of Pineapple Peelings Processing into Vinegar by Biotechnology" Pakistan Journal of Biological Sciences, vol. 12(11):859-865, 2009.

(Continued)

*Primary Examiner* — Charles Boyer
(74) *Attorney, Agent, or Firm* — Rothwell, Figg, Ernst & Manbeck, P.C.

(57) ABSTRACT

Described herein are softening compositions comprising fermented fruit solutions and softening agents, methods for making the same, and methods for using the same. The fermented fruit solutions can contain fruit, sugar and water. The softening agent can be selected from the group consisting of soy lecithin, oleic acid, glycerol, and mixtures thereof. The softening compositions can be used to soften article(s) (e.g., using as a fabric softener).

29 Claims, 6 Drawing Sheets

(56) References Cited

FOREIGN PATENT DOCUMENTS

| TW | 200806194 A | 2/2008 |
|---|---|---|
| WO | 2007049831 A1 | 5/2007 |
| WO | 2008013374 A1 | 1/2008 |
| WO | 2012084426 A1 | 6/2012 |

OTHER PUBLICATIONS

Jekle "Fruit wine—traditional Thai style" Pibulsongkram Rajabhat University, Department of Argo-Industry, Faculty of Food and Agricultural Technology, Phitsanulok, 2005, 5 pages.

Feijoo-Siota et al. "Native and Biotechnology Engineered Plant Proteases with Industrial Applications" Food Bioprocess Technol., Springer, 2010, 23 pages.

Balandrin et al. "Natural Plant Chemicals: Sources of Industrial and Medicinal Materials" Science, New Series, vol. 228, No. 4704, 1985, American Association for the Advancement of Science, pp. 1154-1160.

Australian Government, Department of Health and Ageing, Office of the Gene Technology Regulator "The Biology of *Ananas comosus* var. *comosus* (Pineapple)", Version 2, 2008, 43 pages.

Martinyz "How to make your own Eco-Enzyme Detergent" 2011, printed from http://martinyz.hubpages.com/hub/How-to-make-your-own-Eco-Enzyme-Detergent, on Sep. 5, 2013, 3 pages.

Lee "Citrus Enzyme Cleaner Recipe" 2012, printed from http://www.ecokaren.com/2012/05/citrus-enzyme-cleaner-recipe/, on Sep. 6, 2013, 4 pages.

Office Action dated Feb. 25, 2016, in U.S. Appl. No. 14/768,712, 14 pages.

Office Action dated Feb. 25, 2016, in U.S. Appl. No. 14/768,717, 14 pages.

Office Action dated Feb. 26, 2016, in U.S. Appl. No. 14/768,719, 14 pages.

Office Action issued in Taiwanese Patent Application No. 103132668 on Dec. 13, 2016 along with English translation, 16 pages.

"Research of production for fermented solutions from fruit peels and applications thereof," Reports on results of Competition regarding Specific Subjects under Practice for Domestic Vocational High School Students, year 2012. Pei-Lin Li. etc., with English translation, 47 pages.

Office Action issued in Taiwanese Patent Application No. 103132662 on Oct. 27, 2016 along with English translation, 8 pages.

Notice of Allowance issued in Taiwanese Patent Application No. 103132667 on Nov. 28, 2016, along with English translation of search report, 5 pages.

Method 600                                         FIG. 6
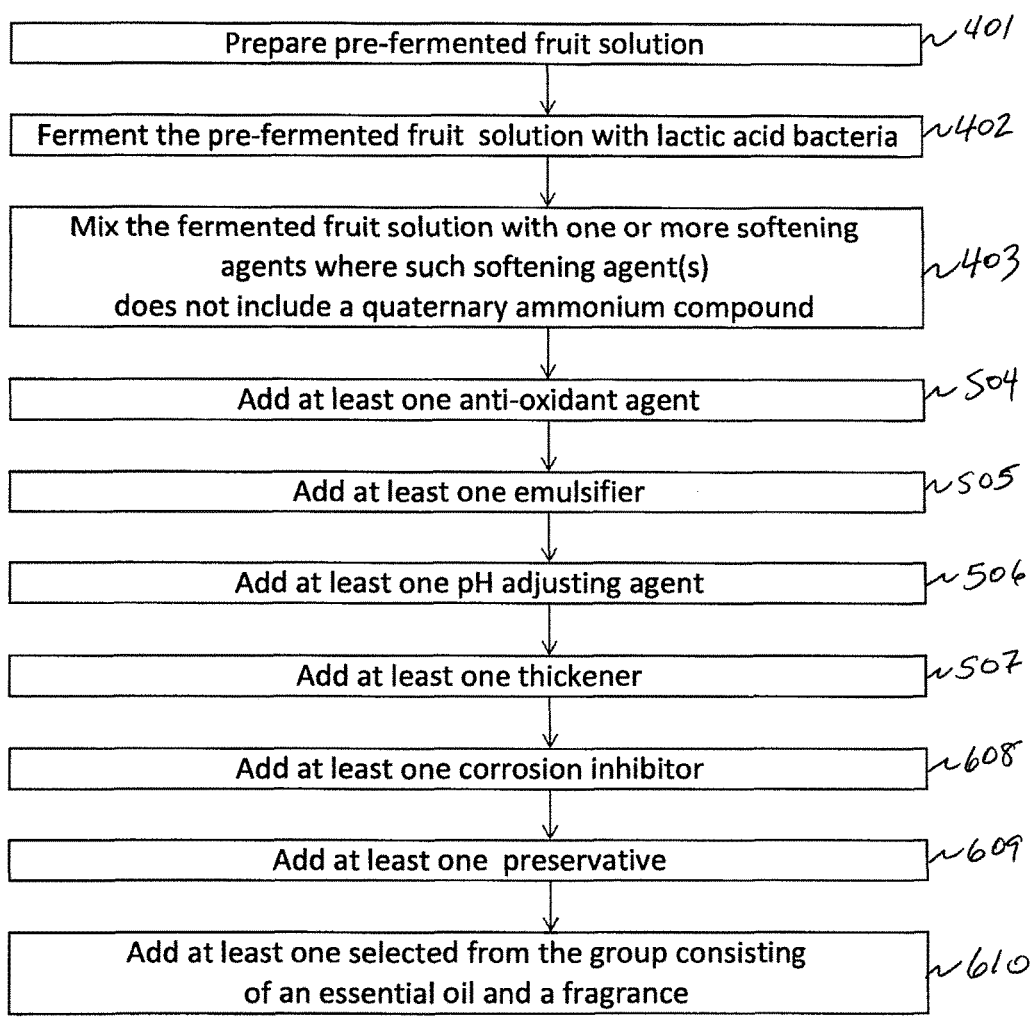

SOFTENING COMPOSITIONS INCLUDING FERMENTED FRUIT SOLUTIONS AND METHODS FOR MAKING AND USING THE SAME

CROSS REFERENCE TO RELATED APPLICATION(S)

This application is a continuation of U.S. application Ser. No. 14/768,715, which is a 35 U.S.C. §371 National Phase Entry Application from PCT/IB2014/061567, filed May 20, 2014, designating the United States, and also claims the benefit of International Application No. PCT/IB2013/002069, filed Sep. 20, 2013. The disclosures of all applications are incorporated herein in their entirety by reference.

TECHNICAL FIELD

The present invention relates generally to softening compositions and, more particularly, to softening compositions comprising fermented fruit solutions, methods for making the same, and methods for using the same (for example, using as a fabric softener).

BACKGROUND

Softening products are commonly used in day to day life—for example, as fabric softener products used by retail consumers or fabric softeners used on a larger scale by companies and institutions such as hotels, hospitals and so forth for items such as sheets, towels, blankets and other types of fabric and material. All major fabric softener products sold throughout the world today use a relatively toxic (to either health and/or to the environment) mix of chemicals as almost all brands contain certain ingredients derived from petrochemicals and/or quaternary ammonium compounds. Products derived from petrochemicals may be harmful since either the final mix of ingredients may contain toxic chemicals and/or the manufacture of these products also may result in the production of harmful by-products. Furthermore, all major brands of fabric softeners, even many small brands which define their products as "natural," use quaternary ammonium compounds. Those calling themselves as natural may derive the quaternary ammonium compounds from natural sources.

Quaternary ammonium compounds have been associated with numerous health problems: allergies, asthma, respiratory issues, contact dermatitis, etc. Numerous references discuss the health risks associated with quaternary ammonium compounds, including references from the Environmental Working Group, which ranks quaternary ammonium compounds with its lowest rating (an F), which it defines as "Highest Concern" "Potentially significant hazards to health or the environment" with "High Concern Skin Allergies & Irritation" and "High Concern Environment" " . . . potential for skin irritation/allergies/damage; acute aquatic toxicity; respiratory effects". See http://www.ewg.org/guides/substance_groups/39. Further, the Environmental Working Group has stated that "Quaternary ammonium compounds ("quats") . . . , found in antibacterial spray cleaners and fabric softeners, can cause asthma." See http://www.ewg.org/guides/cleaners/content/findings.

Furthermore, a type of quaternary ammonium compound called Quaternium-15 has been listed as an allergen under the U.S. FDA approved patch test (T.R.U.E. Test® http://www.truetest.com/commonallergens.aspx) and by the European Society of Contact Dermatitis (http://www.escd.org/aims/standard_series/European_Standard.pdf). A prevalent theory of allergies is that if someone is allergic to one chemical, they may have cross reactions to related chemicals, therefore someone allergic to the known allergen Quaternium-15 may be allergic to other quaternary ammonium compounds.

Given that conventional softening products typically contain quaternary ammonium compounds which are associated with health and environmental issues, and given that on top of this many products also contain toxins related to petrochemicals, there is a need for natural softening products which contain neither quaternary ammonium compounds nor contain toxins related to petrochemicals.

SUMMARY OF THE INVENTION

The present invention provides for natural softening compositions comprising fermented fruit solutions and softening agents which are not quaternary ammonium compounds. The fermented fruit solutions help to dissolve impurities as a natural surfactant and act synergistically with the softening agents which are not quaternary ammonium compounds. The softening compositions of the present invention, which are without quaternary ammonium compounds, have been shown to both soften fabrics on an absolute basis, and have been shown to soften fabrics better than both (a) those brands portraying themselves as 100% natural which do not list in their ingredient list a quaternary ammonium compound and (b) a natural fluid, which is sometimes used in lieu of conventional fabric softeners.

Embodiments of the present invention include softening compositions. The softening compositions comprise a fermented fruit solution. The fermented fruit solution has a total acid content that is greater than or equal to 2.0%. The fermented fruit solution is prepared by fermenting a pre-fermented fruit solution with lactic acid bacteria. The pre-fermented fruit solution comprises about 2 to about 20 weight percent of a sugar based on the total weight of the pre-fermented fruit solution. The pre-fermented fruit solution further comprises about 20 to about 50 weight percent of a fruit puree based on the total weight of the pre-fermented fruit solution, wherein the fruit puree comprises more than 90% pineapple fruit. The pre-fermented fruit solution further comprises about 30 to about 75 weight percent of a water based on the total weight of the pre-fermented fruit solution. The pH of the pre-fermented fruit solution is about 5.5 to about 9.0. The brix level of the pre-fermented fruit solution is about 12% to about 24%. The softening composition also includes one or more softening agents which are not quaternary ammonium compounds. The total weight percent of the one or more softening agents which are not quaternary ammonium compounds is about 2 to about 18 weight percent based on the total weight of the composition.

Embodiments of the present invention include methods of making softening compositions. The method comprises preparing a pre-fermented fruit solution. The pre-fermented fruit solution comprises about 2 to about 20 weight percent of a sugar based on the total weight of the pre-fermented fruit solution. The pre-fermented fruit solution further comprises about 20 to about 50 weight percent of a fruit puree based on the total weight of the pre-fermented fruit solution, wherein the fruit puree comprises more than 90% pineapple fruit. The pre-fermented fruit solution further comprises about 30 to about 75 weight percent of a water based on the total weight of the pre-fermented fruit solution. The pH of the pre-fermented fruit solution is about 5.5 to about 9.0. The brix level of the pre-fermented fruit solution is about 12% to about 24%. The method further comprises fermenting the pre-fermented fruit solution with lactic acid bacteria to create a fermented fruit solution with a total acid content of greater than or equal to 2.0%. The method further comprises mixing the fermented fruit solution with one or more softening agents wherein the one or more softening agents does not include a quaternary ammonium compound and wherein the total weight percent of the one or more softening agents which does not include a quaternary ammonium compound is about 2 to about 18 weight percent based on the total weight of the composition.

Embodiments of the present invention include methods for softening an article with a softening composition comprising a fermented fruit solution and one or more softening agents which are not quaternary ammonium compounds.

BRIEF DESCRIPTION OF THE FIGURES

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein.

FIG. 6 illustrates a flow diagram of a third exemplary method of making softening compositions in accordance with exemplary embodiments of the present invention.

DETAILED DESCRIPTION

Figure 1:
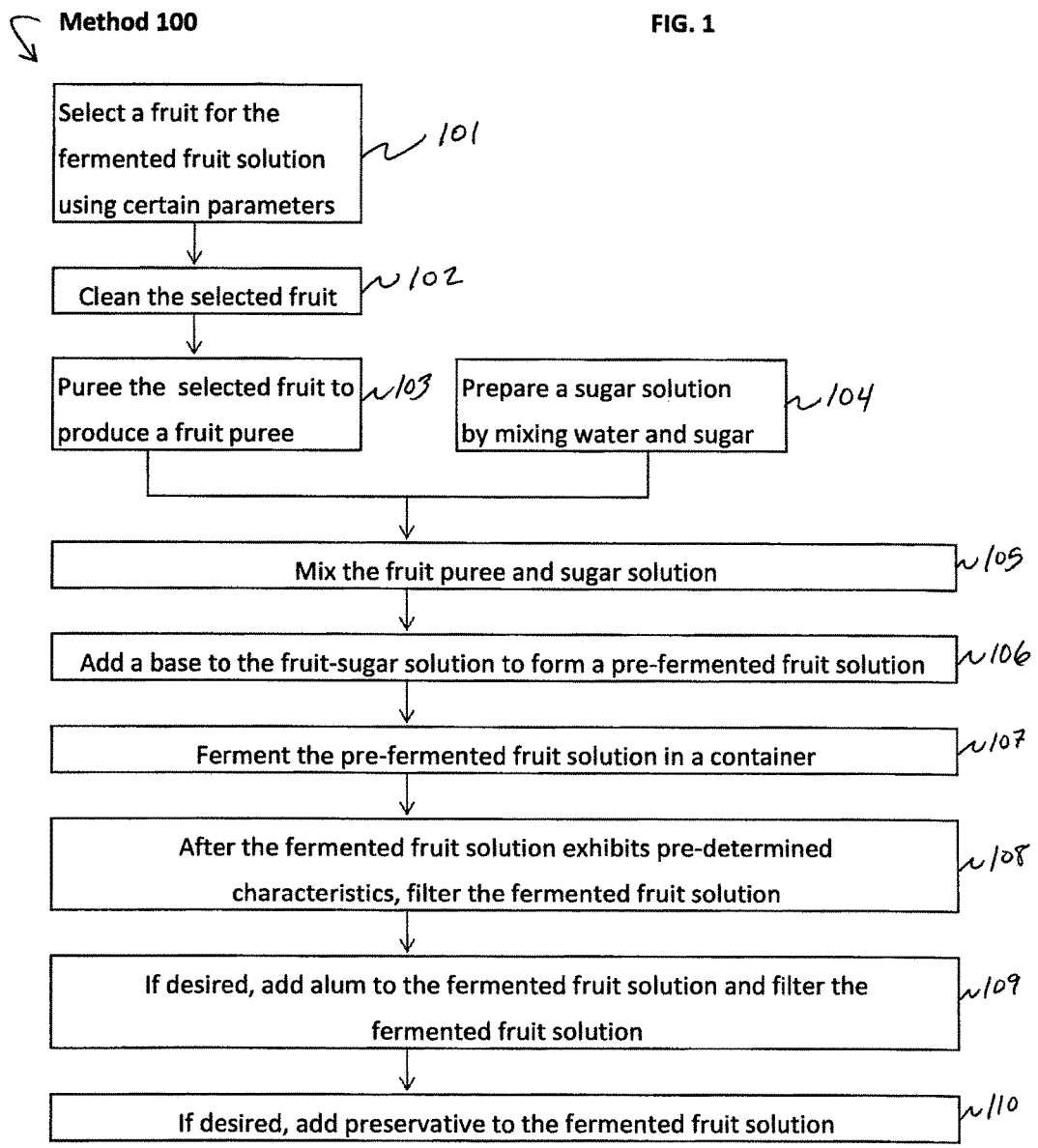
FIG. 1 illustrates a flow diagram of an exemplary method of making fermented fruit solutions in accordance with exemplary embodiments of the present invention.

The present invention relates generally to natural softening compositions comprising fermented fruit solutions, methods for making the same, and methods for using the same. The fermented fruit solutions can contain fruit, sugar and water. As defined herein, softening compositions include, but are not limited to, fabric softeners and related products.

Embodiments of the present invention include fermented fruit solutions for use with softening compositions. The fermented fruit solutions can include a pre-fermented fruit solution that is fermented with lactic acid bacteria. The pre-fermented fruit solution is prepared prior to fermentation and may comprise fruit puree, sugar and water in various amounts.

The fruit puree can be a mashed up fruit mixture comprising predominately pineapple. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple. The portion of the fruit mixture that does not comprise pineapple can comprise other fruits such as lime. Any or some or all parts of the pineapple can be used, provided that more than just the crown of the pineapple is used. Preferably, the entirety of the pineapple including the crust/shell minus the crown of the pineapple can be used. Preferably, the brix level of the fruit is greater than or equal to 10%. Even more preferably, the brix level is greater than or equal to 12%.

The pre-fermented fruit solution can comprise fruit puree in amounts from about 20 to about 50 weight percent based on the total weight of pre-fermented fruit solution. More preferably, the pre-fermented fruit solution can comprise fruit puree in amounts from about 35 to about 40 weight percent based on the total weight of pre-fermented fruit solution. Most preferred, the pre-fermented fruit solution comprises 37.5 weight percent of fruit puree based on the total weight of the pre-fermented fruit solution.

The pre-fermented fruit solution also contains a sugar. The sugar can be any sugar including a type of disaccharide, oligosaccharide and/or a type of monosaccharide. The sugar can be in either solid or liquid form. Preferably, the sugar is sucrose. The pre-fermented fruit solution can comprise sugar in amounts from about 2 to about 20 weight percent based on the total weight of pre-fermented fruit solution. More preferably, the pre-fermented fruit solution can comprise sugar in amounts from about 10 to about 15 weight percent based on the total weight of the pre-fermented fruit solution. Even more preferably, the pre-fermented fruit solution can comprise sugar in an amount of about 12.5 weight percent based on the total weight of the pre-fermented fruit solution.

The pre-fermented fruit solution can also comprise water. The pre-fermented fruit solution can comprise water in amounts from about 30 to about 75 weight percent based on the total weight of the pre-fermented fruit solution. The pre-fermented fruit solution can comprise water in amounts from about 40 to about 60 weight percent based on the total weight of pre-fermented fruit solution. More preferably, the pre-fermented fruit solution can comprise water in an amount of about 50 weight percent based on the total weight of the pre-fermented fruit solution.

The brix level of the pre-fermented fruit solution can be between about 12% to about 24%. Additionally, a base can be added to the pre-fermented fruit solution to adjust the pH of the solution. Examples of bases for use with the present invention include sodium hydroxide, potassium hydroxide and alkyl poly glucoside ("APG"). Preferably the pH is adjusted to a pH between 5.5 and 9.0. More preferably, the pH is adjusted to a pH of 6.0 to 8.0.

The pre-fermented fruit solution is fermented with lactic acid bacteria until the total acid content and total sugar content reach preferred levels. The pre-fermented fruit solution can be fermented with lactic acid bacteria naturally produced from the selected fruit. Alternatively or additionally, a lactic acid bacteria starter can be added to the pre-fermented fruit solution. Preferably, the pre-fermented fruit solution is fermented until the total acid content is greater than or equal to 2%. More preferably, the pre-fermented fruit solution is fermented until the total acid content is greater than or equal to 3%. The total acid content can be measured using a titration method. Preferably, the pre-fermented fruit solution is fermented until the total sugar content is less than or equal to 0.10%. More preferably, the pre-fermented fruit solution is fermented until the total sugar content is less than or equal to 0.05%. The total sugar content can be measured using a dinitrosalicylic colorimetric ("DNS") method. Once such parameters of total sugar and total acid are met, we refer to this solution below as the fermented solution.

The fermented solution is then filtered. After filtering, alum, although not necessary, can be added to the fermented solution to aid with the filtration of sediment from the solution. Alum can be added in an amount ranging from 0.5 to 1.0 weight percent based on the total weight of the solution. After greater than or equal to 24 hours, the sediment can be removed from the solution after the addition of alum.

If a long-lasting product is desired, preservatives, such as potassium metabisulphite, potassium sorbate, and/or sodium benzoate can be added to the fermented solution to stop the fermentation process. If the preservative is potassium metabisulphite, potassium metabisulphite can be added in an amount from about 0.001 to about 0.2 weight percent based on the total weight of the fermented fruit solution. Preferably, potassium metabisulphite can be added in an amount from about 0.01 to about 0.1 weight percent based on the total weight of the fermented fruit solution. If the preservative is a mixture of potassium sorbate and sodium benzoate, potassium sorbate can be added in an amount from about 0.1 to about 1 weight percent based on the total weight of the fermented fruit solution and sodium benzoate can be added in an amount from about 0.01 to about 0.1 weight percent based on the total weight of the fermented fruit solution.

Embodiments of the present invention also include methods of making fermented fruit solutions for use with softening compositions.

Referring now to FIG. 1, a flow diagram illustrating the steps of a method of making fermented fruit solutions in accordance with exemplary embodiments of the present invention is provided. In an embodiment of the present invention, method 100 includes selecting one fruit (step 101). The fruit used is predominately pineapple. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple. The remaining percentage of the fruit puree can comprise an additional fruit such as lime. Any or some or all parts of the pineapple can be used, provide that more than just the crown of the pineapple is used. Preferably, the entirety of the pineapple including the crust/shell minus the crown of the pineapple can be used.

In selecting the fruit to puree, it is preferable that the brix level of the fruit is greater than or equal to 10%. Even more preferably, the brix level must be greater than or equal to 12%. The brix level of the fruit can be determined by measuring the brix level of the fruit puree using a refractometer.

Next, in method 100, the selected fruit can be cleaned (step 102). The fruit can be cleaned by soaking the fruit in water with already created fermented fruit solution. As the final fermented fruit solution is a cleaning solution, the fermented fruit solution can be used to effectively clean the fruit for future production. The fermented fruit solution is a natural surfactant that helps clean pesticides and other impurities within the fruit. Additionally, the fermented fruit solution contains lactic acid bacteria, to aid with the fermentation of the pre-fermented fruit solution.

The weight percent of the fermented fruit solution used for cleaning the fruit can be greater than or equal to 5% fermented fruit solution, with the remaining amount comprising water. The total acid content of the fermented fruit solution can be greater than or equal to 2%. The fruit can be soaked in the fermented fruit solution for greater than or equal to three hours.

Alternatively, but less preferably, the fruit can be cleaned with only water. The fruit can be soaked in the solution of water for greater than or equal to 24 hours.

Next, the method of making fermented fruit solutions can include pureeing a fruit to produce a fruit puree (step 103). The fruit puree can be obtained by grinding the fruit into a puree. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple.

As illustrated in FIG. 1, the method of making fermented fruit solutions can include preparing a sugar solution by mixing water and sugar (step 104). The sugar solution can be prepared by mixing about 3 to about 40 weight percent of a sugar with about 60 to about 97 weight percent of a water to form a sugar solution. Preferably, the sugar solution can be prepared by mixing about 14 to about 27 weight percent of a sugar with about 73 to about 86 weight percent of a water. More preferably, the sugar solution can be prepared by mixing about 20 weight percent of a sugar with about 80 weight percent of a water. The sugar and water can be mixed with an electric stirrer. The sugar can be any sugar including a type of disaccharide, oligosaccharide and/or a type of monosaccharide. The sugar can be in either solid or liquid form. Preferably, the sugar is sucrose. The brix level of the sugar solution preferably is greater than or equal to 19%. The brix level of the sugar solution can be determined by using a refractometer.

As illustrated in FIG. 1, the method of making fermented fruit solutions can include mixing the fruit puree and sugar solution (step 105). The mixture can be prepared by mixing about 20 to about 50 weight percent of the fruit puree with about 50 to about 80 weight percent of the sugar solution to produce a fruit-sugar solution, wherein the weight percents are based on the total weight of the fruit-sugar solution. Preferably, the mixture can be prepared by mixing about 35 to about 38 weight percent of the fruit puree with about 62 to about 65 weight percent of the sugar solution. More preferably, the mixture can be prepared by mixing about 37.5 weight percent of the fruit puree with about 62.5 weight percent of the sugar solution. The fruit puree and sugar solution can be mixed with an electric stirrer.

As illustrated in FIG. 1, the method of making fermented fruit solutions can include adding a base to the fruit-sugar solution to form a pre-fermented fruit solution (step 106). A base can be added to the fruit-sugar solution such that it produces a pre-fermented fruit solution with a pH of about 5.5 to about 9.0. Preferably, a base can be added to the fruit-sugar solution such that it produces a pre-fermented fruit solution with a pH of about 6.0 to about 8.0. The base can be selected from the group consisting of sodium hydroxide, potassium hydroxide and APG. After addition of the base, the pre-fermented fruit solution preferably has a brix level of about 12% to about 24%. More preferably, the pre-fermented fruit solution has a brix level of about 15% to about 24%. The brix level of the pre-fermented fruit solution can be determined by using a refractometer.

As illustrated in FIG. 1, the method of making fermented fruit solutions can include fermenting the pre-fermented fruit solution in a closed container (step 107). In certain embodiments of the invention, the pre-fermented fruit solution can fill the container in an amount between about 85% to about 90%. In certain embodiments of the invention, the container is a 200 liter polyethylene plastic tank with a lid. The remainder of the container can be air. The container can be secured with a clamp device to ensure that the pre-fermented fruit solution is not exposed to outside environmental conditions or contaminants. The container can be stored at ambient temperature in tropical climates, for instance at temperatures ranging from 27 to 45° C.

The pre-fermented fruit solution can be allowed to ferment until the solution exhibits certain characteristics. The characteristics that can be observed to aid in the determination of when to stop fermentation can include the total sugar content, total acid content, electrical conductivity, total microbial count, lactic acid bacteria count, and/or yeast and mold count. The characteristics of the pre-fermented fruit solution can be observed at set intervals. The characteristics can be observed on a weekly or monthly basis.

The pre-fermented fruit solution can be fermented until it exhibits a total sugar content that is close to or equal to zero percent. Preferably, the pre-fermented fruit solution is allowed to ferment until the total sugar content is less than or equal to 0.10%. More preferably, the pre-fermented solution is allowed to ferment until the total sugar content is less than or equal to 0.05%.

The pre-fermented fruit solution can be fermented until it exhibits a total acid content that reaches a certain level. Preferably, the pre-fermented fruit solution is allowed to ferment until the total acid content is greater than or equal to 2%. More preferably, the pre-fermented solution is allowed to ferment until the total acid content is greater than or equal to 3%.

As illustrated in FIG. 1, after the solution exhibits certain pre-determined characteristics, the fermented fruit solution can be filtered (step 108). The fermented fruit solution can be filtered with a filter to separate crusts. An example of a filter for use with the present invention is a cloth filter.

Following filtration, alum, although not necessary, can be added to the fermented fruit solution and the fermented fruit solution can once again be filtered (step 109). Alum can be added to the fermented fruit solution to aid with the settling of sediment. Alum can be added in an amount ranging from about 0.5 weight percent to 1.0 weight percent based on the total weight of the fermented fruit solution. After addition of alum, the fermented fruit solution can sit for greater than or equal to 24 hours. The fermented fruit solution can then be filtered. The fermented fruit solution can be filtered using a filter. An example of a filter for use with the present invention is a cloth filter.

If desired for a long-lasting product, as illustrated in FIG. 1, the method of making fermented fruit solutions can include adding a preservative, such as potassium metabisulphite, potassium sorbate, and/or sodium benzoate to the fermented fruit solution (step 110). Such preservative (s) can be added to the fermented fruit solution once the solution exhibits certain characteristics, as described above. The preservative(s) can be added to stop the fermentation process. If the preservative is potassium metabisulphite, potassium metabisulphite can be added in an amount from about 0.001 to about 0.2 weight percent based on the total weight of the fermented fruit solution. Preferably, potassium metabisulphite can be added in an amount from about 0.01 to about 0.1 weight percent based on the total weight of the fermented fruit solution. If the preservative is a mixture of potassium sorbate and sodium benzoate, potassium sorbate can be added in an amount from about 0.1 to about 1 weight percent based on the total weight of the fermented fruit solution and sodium benzoate can be added in an amount from about 0.01 to about 0.1 weight percent based on the total weight of the fermented fruit solution. After adding the preservative(s), the fermented fruit solution should be allowed to sit for a minimum of 3 hours.

Following the addition of such preservative(s), if any, the fermented fruit solution can be used in a softening composition. The fermented fruit solution can be used in softening compositions, including for example, fabric softeners and related products.

Figure 2:
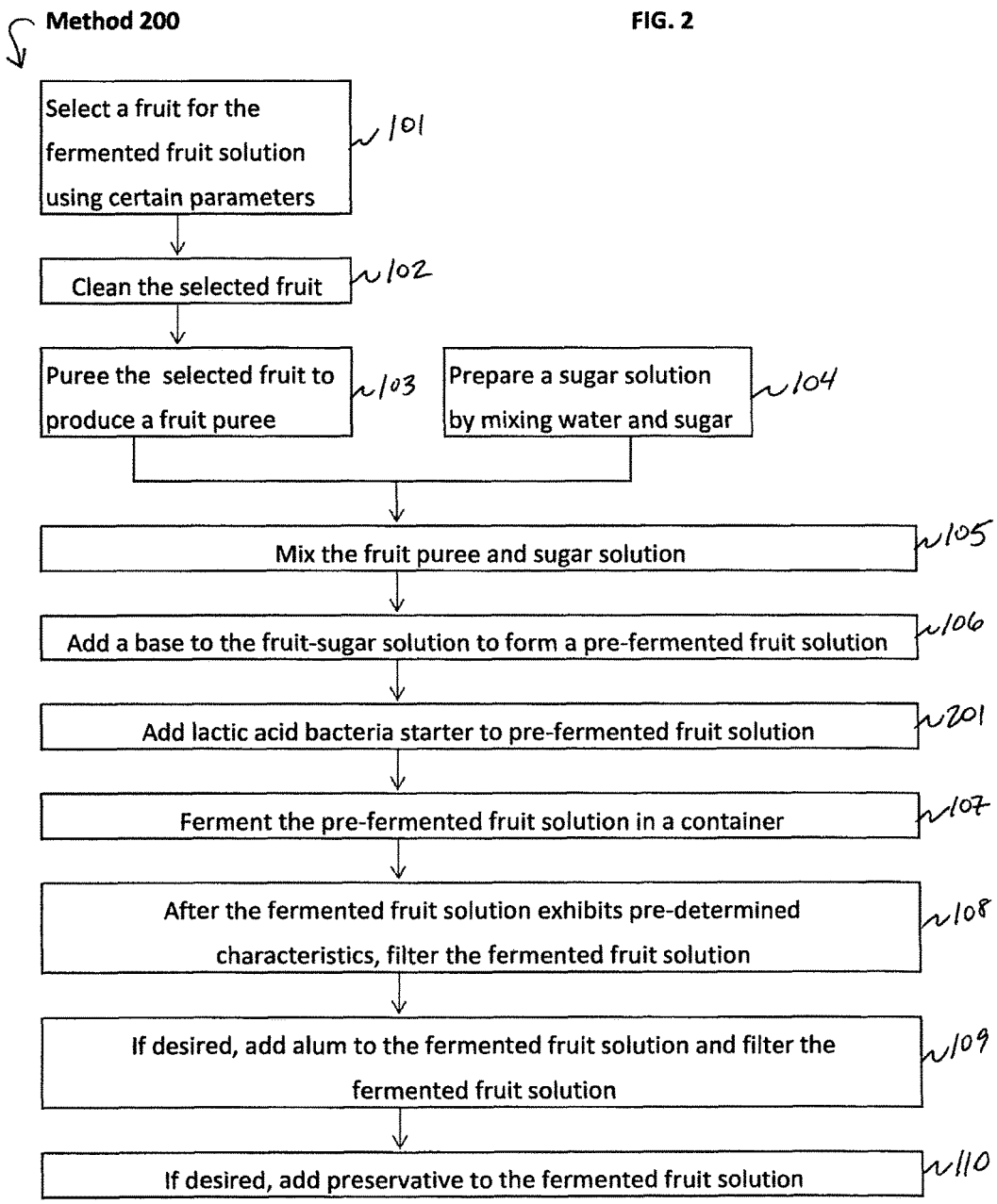
FIG. 2 illustrates a flow diagram of a second exemplary method of making fermented fruit solutions in accordance with exemplary embodiments of the present invention.

Referring now to FIG. 2, a flow diagram illustrating the steps of a method of making fermented fruit solutions in accordance with exemplary embodiments of the present invention is provided. In an embodiment of the present invention, method 200 includes several of the same steps described above in reference to method 100, including steps 101 through 110.

In method 200, as illustrated in FIG. 2, method 200 can include adding lactic acid bacteria starter to the pre-fermented fruit solution (step 201). The lactic acid bacteria starter can be added to the pre-fermented fruit solution to help with fermentation of the pre-fermented fruit solution.

As illustrated in FIG. 2, after step 201, method 200 includes step 107 through step 110.

Figure 3:
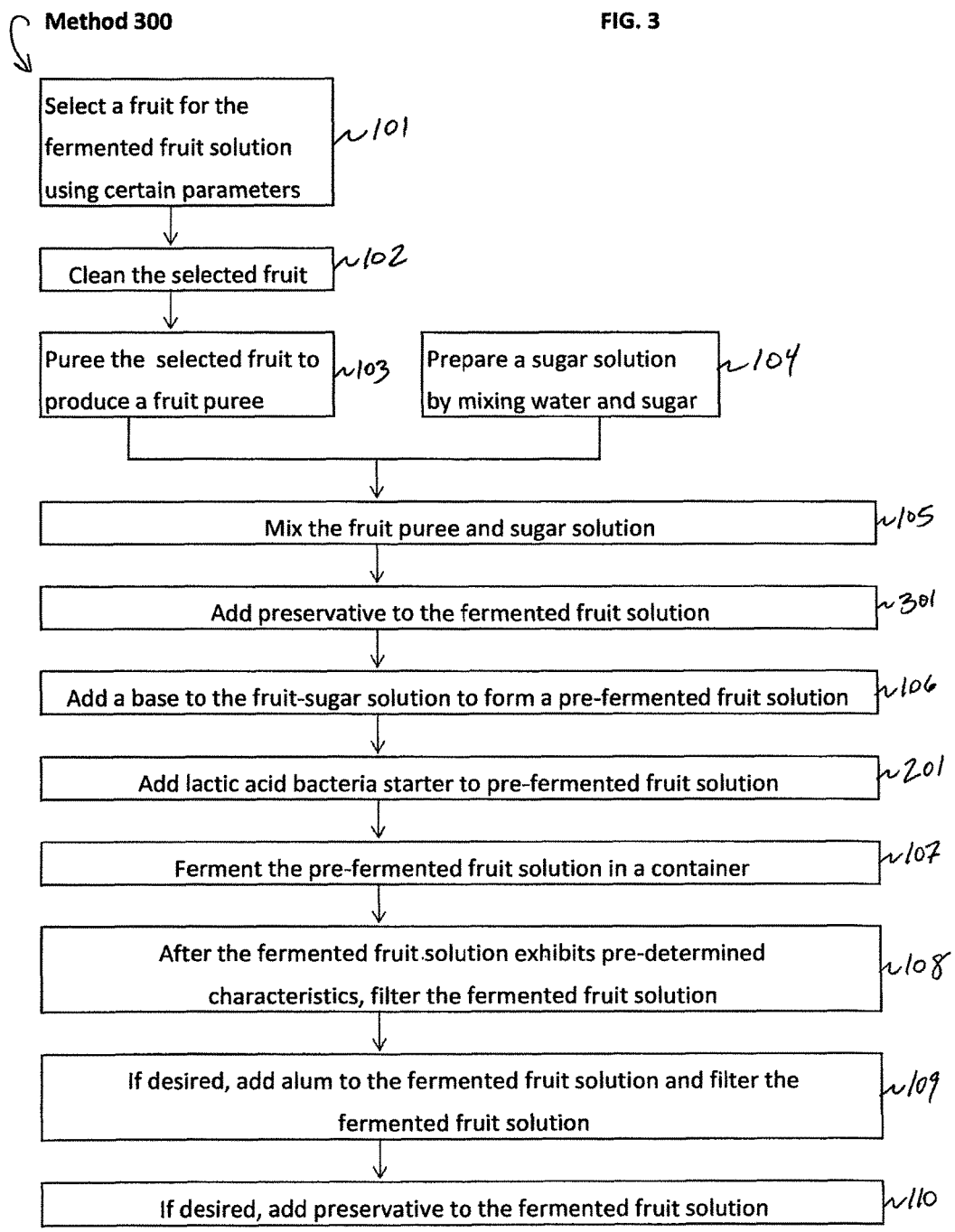
FIG. 3 illustrates a flow diagram of a third exemplary method of making fermented fruit solutions in accordance with exemplary embodiments of the present invention.

Referring now to FIG. 3, a flow diagram illustrating the steps of a method of making fermented fruit solutions in accordance with exemplary embodiments of the present invention is provided. In an embodiment of the present invention, method 300 includes several of the same steps described above in reference to method 200, including steps 101 through 110.

As illustrated in FIG. 3, method 300 can include adding a preservative(s), such as potassium metabisulphite, potassium sorbate, and/or sodium benzoate to the fruit-sugar solution after the fruit sugar solution is prepared by mixing the fruit puree and sugar solution (step 301). Such preservative(s) can be used to kill micro-organisms in the fruit-sugar solution including yeast and mold. After adding the preservative and adjusting pH of the fruit-sugar solution (see step 106), lactic acid bacteria can be added (step 201). As illustrated in FIG. 3, after step 201, method 300 includes steps 107 through steps 110 from methods 100 and 200.

Embodiments of the present invention also include methods of softening an article with a softening composition comprising a fermented fruit solution. Following preparation of the fermented fruit solutions described above, the fermented fruit solutions can be used to soften an article. Methods of the invention can comprise using a softening composition with a fermented fruit solution to soften an article.

Embodiments of the present invention include softening compositions comprising fermented fruit solutions and softening agents wherein the softening agents do not include quaternary ammonium compounds. The softening compositions can include a fermented fruit solution such as the above described fermented fruit solutions. The softening compositions can be used as fabric softeners and related products.

The softening compositions can include one or more softening agents wherein the one or more softening agents does not include a quaternary ammonium compound. In preferred embodiments of the present invention, the one or more softening agents wherein the one or more softening agents does not include a quaternary ammonium compound is selected from the group consisting of soy lecithin, oleic acid, glycerol and mixtures thereof. Preferably, the total weight percent of the one or more softening agents, wherein the one or more softening agents does not include a quaternary ammonium compound, is about 2 to about 18 weight percent based on the total weight of the composition. More preferably, the total weight percent of the one or more softening agents wherein the one or more softening agents does not include a quaternary ammonium compound is about 3 to about 12.5 weight percent. Even more preferably, the total weight percent of the one or more softening agents wherein the one or more softening agents does not include a quaternary ammonium compound is about 5.5 to about 10 weight percent.

In certain embodiments of the present invention, the one or more softening agents wherein the one or more softening agents does not include a quaternary ammonium compound is a mixture of soy lecithin, oleic acid, and glycerol. In embodiments where the softening composition comprises a mixture of soy lecithin, oleic acid, and glycerol, soy lecithin can be present in amount of about 1 to about 3 weight percent based on the total weight of the composition, oleic acid can be present in amount of about 1 to about 5 weight percent based on the total weight of the composition and glycerol can be present in an amount of about 1 to about 10 weight percent based on the total weight of the composition. More preferably, in embodiments where the softening composition comprises a mixture of soy lecithin, oleic acid, and glycerol, soy lecithin can be present in amount of about 1 to about 2.5 weight percent based on the total weight of the composition, oleic acid can be present in amount of about 1 to about 3 weight percent based on the total weight of the composition and glycerol can be present in an amount of about 1 to about 7 weight percent based on the total weight of the composition. Even more preferably, in embodiments where the softening composition comprises a mixture of soy lecithin, oleic acid, and glycerol, soy lecithin can be present in amount of about 1.5 to about 2 weight percent based on the total weight of the composition, oleic acid can be present in amount of about 2 to about 3 weight percent based on the total weight of the composition and glycerol can be present in an amount of about 2 to about 5 weight percent based on the total weight of the composition.

The softening compositions can include at least one anti-oxidant agent. In preferred embodiments of the invention, the at least one anti-oxidant agent is vitamin E. Preferably, the at least one anti-oxidant agent is present in an amount of about 0.2 to about 1 weight percent based on the total weight of the composition.

The softening compositions can include at least one emulsifier. In preferred embodiments of the present invention, the at least one emulsifier is selected from the group consisting of PEG-60 hydrogenated castor oil, polyoxyethylene (20) sorbitan monooleate, sorbitan monooleate, and mixtures thereof. Preferably, the at least one emulsifier is present in an amount of about 2 to about 5 weight percent based on the total weight percent of the composition.

The softening compositions can include at least one pH adjusting agent. In preferred embodiments of the present invention, the at least one pH adjusting agent is selected from the group consisting of citric acid, lactic acid and mixtures thereof. Preferably, the at least one pH adjusting agent is present in an amount of about 2 to about 5 weight percent based on the total weight of the composition.

The softening compositions can include at least one thickener. In preferred embodiments of the invention, the thickener is at least one selected from the group consisting of natural gums, sodium chloride and mixtures thereof. Examples of natural gums that can be used with the present invention include guar gum, xantham gum, and gum arabic. Preferably, the thickener is present in an amount of about 0.1 to about 2 weight percent based on the total weight of the composition.

The softening compositions can include at least one corrosion inhibitor. In preferred embodiments of the present invention, the at least one corrosion inhibitor is selected from the group consisting of gum arabic, sodium polyaspartate and mixtures thereof. Preferably, the at least one corrosion inhibitor is present in an amount of about 0.1 to about 2.5 weight percent based on the total weight of the composition.

The softening compositions can also include a preservative. Examples of preservatives for use with the present invention include boric acid, benzoic acid, potassium sorbate, nisin, natamycin, and mixtures thereof. Preferably, the preservative is selected from the group consisting of potassium sorbate, nisin, natamycin, and mixtures thereof. If boric acid, the preservative can be present in an amount not greater than about 2 weight percent based on the total weight of the composition. If not boric acid, the preservative can be present in an amount of not greater than about 1 weight percent based on the total weight of the composition.

The softening compositions can also include an essential oil and/or a fragrance.

The softening compositions can also include water. The remainder of the weight percent can be water.

Figure 4:
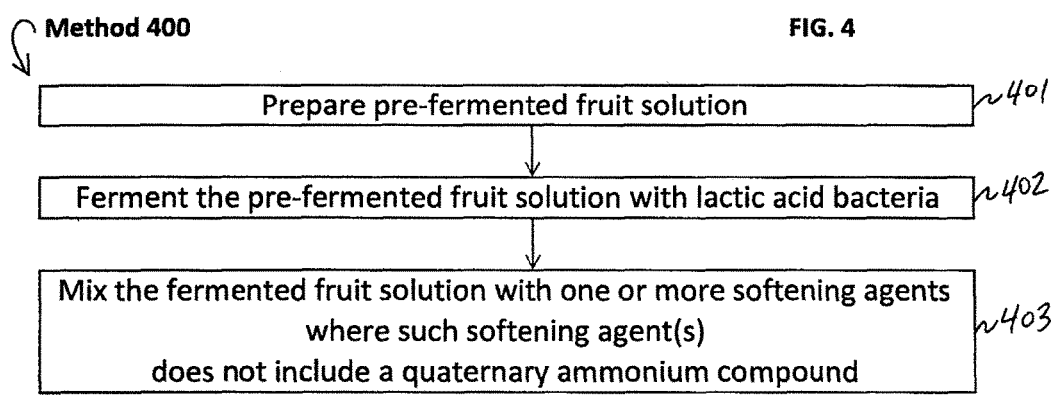
FIG. 4 illustrates a flow diagram of an exemplary method of making softening compositions in accordance with exemplary embodiments of the present invention.

Embodiments of the present invention include methods of making softening compositions. Referring now to FIG. 4, a flow diagram illustrating the steps of a method of making softening compositions in accordance with exemplary embodiments of the present invention is provided. In an embodiment of the present invention, method 400 includes preparing a pre-fermented fruit solution (step 401). The pre-fermented fruit solution can be prepared in accordance with the above described methods, for example methods 100, 200 and/or 300. As described in detail above, the pre-fermented fruit solution is prepared prior to fermentation and may comprise fruit puree, sugar and water in various amounts.

Next, in method 400, the pre-fermented fruit solution can be fermented with lactic acid bacteria to create a fermented fruit solution (step 402). The pre-fermented fruit solution can be fermented as described in detail above, for example in methods 100, 200 and/or 300.

Next, in method 400, the fermented fruit solution can be mixed with one or more softening agents wherein the one or more softening agents does not include a quaternary ammonium compound (step 403). The total weight percent of the one or more softening agents, wherein the one or more softening agents does not include a quaternary ammonium compound, can be about 2 to about 18 weight percent based on the total weight of the composition. In certain embodiments of the claimed invention, the mixing can be performed at temperatures between 25° C. to 35° C. A high speed mixer or homogenizer can be used to perform the mixing. In preferred embodiments of the present invention, the one or more softening agents wherein the one or more softening agents does not include a quaternary ammonium compound is selected from the group consisting of soy lecithin, oleic acid, glycerol and mixtures thereof. Preferably, the total weight percent of the one or more softening agents wherein the one or more softening agents does not include a quaternary ammonium compound is about 2 to about 18 weight percent based on the total weight of the composition. More preferably, the one or more softening agents wherein the one or more softening agents does not include a quaternary ammonium compound is used in an amount of about 3 to about 12.5 weight percent. Even more preferably, the one or more softening agents wherein the one or more softening agents does not include a quaternary ammonium compound is used in an amount of about 5.5 to about 10 weight percent.

In certain embodiments of the present invention, the one or more softening agents wherein the one or more softening agents does not include a quaternary ammonium compound is a mixture of soy lecithin, oleic acid and glycerol. In embodiments where the softening composition comprises a mixture of soy lecithin, oleic acid, and glycerol, soy lecithin can be used in amount of about 1 to about 3 weight percent based on the total weight of the composition, oleic acid can be used in amount of about 1 to about 5 weight percent based on the total weight of the composition and glycerol can be used in an amount of about 1 to about 10 weight percent based on the total weight of the composition. More preferably, in embodiments where the softening composition comprises a mixture of soy lecithin, oleic acid, and glycerol, soy lecithin can be used in amount of about 1 to about 2.5 weight percent based on the total weight of the composition, oleic acid can be used in amount of about 1 to about 3 weight percent based on the total weight of the composition and glycerol can be used in an amount of about 1 to about 7 weight percent based on the total weight of the composition. Even more preferably, in embodiments where the softening composition comprises a mixture of soy lecithin, oleic acid, and glycerol, soy lecithin can be used in amount of about 1.5 to about 2 weight percent based on the total weight of the composition, oleic acid can be used in amount of about 2 to about 3 weight percent based on the total weight of the composition and glycerol can be used in an amount of about 2 to about 5 weight percent based on the total weight of the composition.

Figure 5:
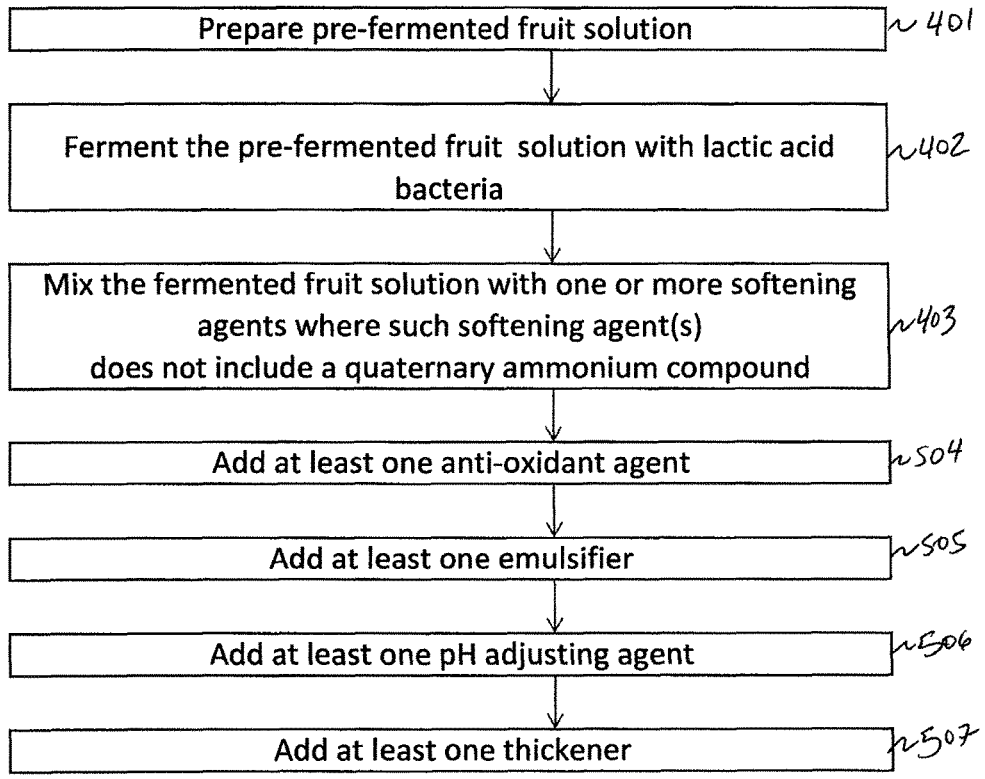
FIG. 5 illustrates a flow diagram of a second exemplary method of making softening compositions in accordance with exemplary embodiments of the present invention.

Referring now to FIG. 5, a flow diagram illustrating the steps of a method of making softening compositions in accordance with exemplary embodiments of the present invention is provided. In an embodiment of the present invention, method 500 includes several of the same steps of method 400, including steps 401, 402, and 403.

Next, in method 500, at least one anti-oxidant agent can be added to the mixture (step 504). In preferred embodiments of the present invention, the at least one anti-oxidant agent is vitamin E. Preferably, the at least one anti-oxidant agent is used in an amount of about 0.2 to about 1 weight percent based on the total weight percent of the composition.

Method 400 can further include adding at least one emulsifier (step 505). The at least one emulsifier can be selected from the group consisting of PEG-60 hydrogenated castor oil, polyoxyethylene (20) sorbitan monooleate, sorbitan monooleate, and mixtures thereof. Preferably, the at least one emulsifier is used in an amount of about 2 to about 5 weight percent based on the total weight of the composition.

Next, in method 500, at least one pH adjusting agent is added to the mixture (step 506). The at least one pH adjusting agent can be selected from the group consisting of citric acid, lactic acid and mixtures thereof. Preferably, the at least one pH adjusting agent is used in an amount of about 2 to about 5 weight percent based on the total weight of the composition.

Method 500 can further include adding a mixture of at least one thickener with water (step 507). In preferred embodiments of the invention, the thickener is at least one selected from the group consisting of natural gums, sodium chloride and mixtures thereof. Examples of natural gums that can be used with the present invention include guar gum, xantham gum, and gum arabic. Preferably, the thickener is used in an amount of about 0.1 to about 2 weight percent based on the total weight of the composition. The thickener can be mixed with water prior to being added. A homogenizer can be used to dissolve xantham gum, guar gum, gum arabic or other natural gums used with the present invention.

Referring now to FIG. 6, a flow diagram illustrating the steps of a method of making softening compositions in accordance with exemplary embodiments of the present invention is provided. In an embodiment of the present invention, method 600 includes several of the same steps of method 500, including steps 401, 402, 403 and steps 504 through 507.

Next, in method 600, at least one corrosion inhibitor is added to the mixture (step 608). In preferred embodiments of the invention, the at least one corrosion inhibitor is at least one selected from the group consisting of gum arabic, sodium polyaspartate and mixtures thereof. Preferably, the at least one corrosion inhibitor is used in an amount of about 0.1 to about 2.5 weight percent based on the total weight of the composition.

Next, in method 600, at least one preservative is added to the mixture (step 609). Examples of preservatives for use with the present invention include boric acid, benzoic acid, potassium sorbate, nisin, natamycin, and mixtures thereof. Preferably the preservative is at least one selected from the group consisting of potassium sorbate, nisin, natamycin, and mixtures thereof. If boric acid, the preservative can be used in an amount not greater than about 2 weight percent based on the total weight of the composition. If not boric acid, the preservative can be used in an amount of not greater than about 1 weight percent based on the total weight of the composition.

Next, in method 600, at least one selected from the group consisting of an essential oil and a fragrance is added to the mixture (step 610).

Embodiments of the present invention also include methods of softening an article with a softening composition comprising a fermented fruit solution and one or more softening agents wherein the one or more softening agents does not include a quaternary ammonium compound. Following preparation of the softening compositions described above, the softening compositions can be used to soften an article.

The following examples illustrate certain embodiments of the invention without limitation.

EXAMPLES

Fermented fruit solutions were prepared in accordance with the methods described in detail above. The fermented fruit solutions were prepared similarly except for the composition of the pre-fermented fruit solution. Table 1 provides the components of Examples 1-3:

TABLE 1

|  | Example 1 | Example 2 | Example 3 |
| --- | --- | --- | --- |
| Sucrose | 12.5% | 11.1% | 10% |
| Pineapple Puree | 37.5% | 33.3% | 30% |
| Water | 50.0% | 55.6% | 60% |

All concentrations are weight percent, based on the total weight of the pre-fermented fruit composition.

After preparation of the fermented fruit solutions, the pH, total sugar content and total acid content was measured after 2.5 months. Three different samples of each example were measured. The results of these measurements are provided in Table 2.

TABLE 2

|  | pH | Total Sugar Content (%) | Total Acid Content (%) |
| --- | --- | --- | --- |
| Example 1A | 3.09 | 0.04 | 3.19 |
| Example 1B | 3.19 | 0.03 | 3.07 |
| Example 1C | 3.17 | 1.62 | 3.10 |
| Example 2A | 3.11 | 1.40 | 3.06 |
| Example 2B | 3.08 | 0.10 | 2.28 |
| Example 2C | 3.15 | 0.11 | 2.28 |
| Example 3A | 3.11 | 0.13 | 2.27 |

TABLE 2-continued

|  | pH | Total Sugar Content (%) | Total Acid Content (%) |
| --- | --- | --- | --- |
| Example 3B | 3.16 | 0.15 | 2.25 |
| Example 3C | 3.13 | 0.14 | 2.26 |

As is illustrated in Table 2, the total acid content of Example 1 was surprisingly higher than the total acid content of the other examples. Thus, it appears that the weight percents of sucrose, pineapple and water, as used in Example 1 of the present invention result in superior cleaning compositions. Specifically, a ratio of sugar:fruit:water of 1:3:4 appears to produce superior cleaning compositions.

Additional fermented fruit solutions were prepared in accordance with the methods described in detail above. In Examples 4-33, the pre-fermented fruit solutions were all prepared using a sugar:fruit:water ratio of 1:3:4. In Examples 4-18, the initial brix level of the pineapple used to prepare the pineapple puree was not measured. Rather, all pineapples, regardless of brix level were used for Examples 4-18. In Examples 19-33, the selected pineapples included a brix level of greater than or equal to 12%.

The initial brix level of the pre-fermented fruit solution was measured at day 0. After preparation of the fermented fruit solutions, the pH, total sugar content ("TS") and total acid content ("TA") of the fermented fruit solutions were measured after 1.5 months. Additionally, the pH and total acid content ("TA") of the fermented fruit solutions were measured after 2 months. Finally, the pH, total acid content ("TA"), electric conductivity ("EC") and temperature of the fermented fruit solutions were measured after 3 months. The results of these measurements are provided in Table 3.

TABLE 3

| Example No. | Day 0 Brix Level (%) | 1.5 Months | | | 2 Months | | 3 Months | | | |
| --- | --- | --- | --- | --- | --- | --- | --- | --- | --- | --- |
|  |  | pH | TS (%) | TA (%) | pH | TA (%) | pH | TA (%) | EC (µS) | Temp (° C.) |
| 4 | 16.0 | 2.90 | 0.02 | 3.51 | 3.10 | 3.47 | 3.00 | 3.38 | 2570 | 33.0 |
| 5 | 16.7 | 3.00 | 0.05 | 2.84 | 3.00 | 3.47 | 3.00 | 3.15 | 2540 | 33.0 |
| 6 | 13.0 | 3.00 | 0.04 | 3.15 | 3.10 | 3.11 | 3.00 | 3.38 | 2700 | 33.0 |
| 7 | 12.9 | 2.90 | 0.02 | 3.78 | 3.10 | 3.96 | 3.00 | 3.60 | 2550 | 32.5 |
| 8 | 13.0 | 3.00 | 0.03 | 3.06 | 3.20 | 3.51 | 3.00 | 3.06 | 2400 | 33.0 |
| 9 | 14.9 | 3.00 | 0.07 | 3.24 | 3.00 | 3.69 | 3.00 | 3.74 | 2680 | 33.0 |
| 10 | 15.0 | 3.00 | 0.00 | 3.42 | 3.20 | 3.33 | 3.00 | 3.65 | 2630 | 33.0 |
| 11 | 14.2 | 3.00 | 0.00 | 3.15 | 3.10 | 3.87 | 3.00 | 3.38 | 2620 | 33.0 |
| 12 | 14.6 | 3.00 | 0.06 | 3.11 | 3.00 | 3.78 | 3.00 | 3.69 | 2660 | 32.5 |
| 13 | 14.8 | 3.00 | 0.03 | 3.38 | 3.00 | 3.33 | 3.00 | 3.42 | 2730 | 32.5 |
| 14 | 15.8 | 3.00 | 0.03 | 3.42 | 3.10 | 3.87 | 3.00 | 3.60 | 2560 | 33.0 |
| 15 | 18.0 | 3.00 | 0.04 | 3.42 | 3.00 | 3.74 | 3.00 | 3.56 | 2250 | 32.5 |
| 16 | 14.0 | 3.00 | 0.04 | 3.47 | 3.10 | 3.33 | 3.00 | 3.47 | 2730 | 32.5 |
| 17 | 13.7 | 2.90 | 0.02 | 3.51 | 3.00 | 3.29 | 3.00 | 4.23 | 2640 | 32.5 |
| 18 | 13.4 | 3.00 | 0.03 | 3.42 | 3.10 | 4.01 | 3.00 | 3.29 | 2660 | 32.5 |
| 19 | 16.0 | 3.09 | 0.04 | 2.97 | 3.00 | 3.96 | 3.10 | 3.69 | 2910 | 30.0 |
| 20 | 16.8 | 3.08 | 0.04 | 3.38 | 3.00 | 4.05 | 3.10 | 4.23 | 3210 | 30.0 |
| 21 | 16.7 | 3.04 | 0.04 | 3.78 | 3.00 | 4.23 | 3.00 | 4.82 | 2880 | 30.0 |
| 22 | 15.8 | 3.03 | 0.04 | 3.24 | 3.00 | 4.32 | 3.10 | 5.54 | 3270 | 30.0 |
| 23 | 14.6 | 2.95 | 0.04 | 3.65 | 3.00 | 4.19 | 3.10 | 5.27 | 2990 | 30.0 |
| 24 | 16.7 | 2.96 | 0.04 | 4.41 | 3.00 | 4.05 | 3.10 | 5.27 | 3110 | 30.0 |
| 25 | 17.8 | 2.92 | 0.03 | 4.59 | 2.70 | 4.50 | 3.00 | 4.59 | 2980 | 30.0 |
| 26 | 16.3 | 2.98 | 0.05 | 3.60 | 2.90 | 4.14 | 3.00 | 4.73 | 2790 | 30.0 |
| 27 | 17.5 | 2.92 | 0.03 | 3.60 | 2.90 | 3.78 | 3.10 | 4.19 | 2900 | 30.0 |
| 28 | 18.3 | 2.93 | 0.03 | 4.01 | 2.90 | 3.56 | 3.00 | 5.63 | 2940 | 30.0 |
| 29 | 18.6 | 2.92 | 0.05 | 4.37 | 3.00 | 4.10 | 3.10 | 4.86 | 2910 | 30.0 |
| 30 | 17.5 | 2.93 | 0.04 | 4.23 | 3.00 | 3.78 | 3.10 | 4.77 | 3040 | 30.0 |
| 31 | 16.3 | 2.94 | 0.04 | 4.41 | 3.00 | 3.69 | 3.00 | 4.10 | 3090 | 30.0 |
| 32 | 17.6 | 2.90 | 0.05 | 4.41 | 2.90 | 4.19 | 3.00 | 5.67 | 2970 | 30.0 |
| 33 | 16.6 | 2.97 | 0.02 | 3.96 | 3.00 | 3.96 | 3.00 | 4.32 | 3050 | 30.0 |

As is illustrated in Table 3, the total acid content of Examples 19-33 was surprisingly higher than the total acid content of the other examples. In Examples 4-18, the total acid content after 3 months ranged from 3.06% to 4.23% with a mean value of 3.50%. In Examples 19-33, the total acid content after 3 months ranged from 3.69% to 5.67% with a mean value of 4.77%. Thus, the selection of pineapples for the fruit puree with a brix level greater than or equal to 12% results in superior cleaning compositions.

Additional fermented fruit solutions were prepared in accordance with the methods described in detail above. In Examples 34-48, the selected pineapples were washed only with tap water. In Examples 49-63, the selected pineapples were all washed with previously created fermented fruit solutions.

After preparation of the fermented fruit solutions, the pH and brix level were measured at day 0. Additionally, the pH and total acid content ("TA") were measured after 2 days. The pH, total sugar content ("TS"), total acid content ("TA"), and electrical conductivity ("EC") were measured after 1 month. The results of these measurements are provided in Table 4.

TABLE 4

| Example No. | Day 0 | | Day 2 | | 1 Month | | | |
|---|---|---|---|---|---|---|---|---|
| | pH | Brix Level (%) | pH | TA (%) | pH | TS (%) | TA (%) | EC (µS) |
| 34 | 8.10 | 17.9 | 4.00 | 0.77 | 3.00 | 0.0000 | 2.97 | 3670 |
| 35 | 8.10 | 18.2 | 4.00 | 0.85 | 3.00 | 0.0042 | 3.60 | 3190 |
| 36 | 8.00 | 17.6 | 4.00 | 0.85 | 2.93 | 0.0032 | 3.42 | 3040 |
| 37 | 8.40 | 17.6 | 4.00 | 0.77 | 3.00 | 0.0039 | 2.97 | 3160 |
| 38 | 8.30 | 17.6 | 4.00 | 0.85 | 3.00 | 0.0000 | 2.70 | 3700 |
| 39 | 8.20 | 17.9 | 4.00 | 1.08 | 3.00 | 0.0032 | 4.50 | 3010 |
| 40 | 8.20 | 17.9 | 4.00 | 0.90 | 3.00 | 0.0042 | 3.60 | 3160 |
| 41 | 8.50 | 17.6 | 4.00 | 1.13 | 2.90 | 0.0004 | 3.15 | 3030 |
| 42 | 7.10 | 17.2 | 4.00 | 1.04 | 3.00 | 0.0056 | 3.29 | 3490 |
| 43 | 7.40 | 17.9 | 4.00 | 1.04 | 3.00 | 0.0046 | 3.11 | 2950 |
| 44 | 6.40 | 17.2 | 4.00 | 1.04 | 3.00 | 0.0011 | 3.78 | 3820 |
| 45 | 7.10 | 17.8 | 4.00 | 0.68 | 3.00 | 0.0042 | 3.15 | 3640 |
| 46 | 6.70 | 17.2 | 4.00 | 0.63 | 3.00 | 0.0001 | 3.51 | 3610 |
| 47 | 6.70 | 17.6 | 4.00 | 1.26 | 3.00 | 0.0022 | 3.15 | 3420 |
| 48 | 7.40 | 17.7 | 4.00 | 1.22 | 3.00 | 0.0000 | 3.51 | 3540 |
| 49 | 6.70 | 18.6 | — | — | 3.10 | 0.0404 | 5.22 | 3910 |
| 50 | 7.00 | 18.2 | 3.40 | 3.33 | 3.10 | 0.0369 | 4.14 | 3830 |
| 51 | 6.40 | 18.0 | — | — | 3.00 | 0.0321 | 5.04 | 3550 |
| 52 | 6.20 | 17.7 | 3.48 | 3.87 | 3.00 | 0.0547 | 4.32 | 3050 |
| 53 | 6.40 | 17.7 | — | — | 3.10 | 0.0415 | 4.86 | 3600 |
| 54 | 6.10 | 17.5 | 3.50 | 2.07 | 3.00 | 0.0373 | 5.22 | 3560 |
| 55 | 6.10 | 17.5 | 3.40 | 3.24 | 3.00 | 0.0356 | 4.95 | 3440 |
| 56 | 6.20 | 17.8 | — | — | 3.10 | 0.0392 | 5.40 | 3600 |
| 57 | 6.40 | 18.3 | — | — | 3.10 | 0.0356 | 4.68 | 3970 |
| 58 | 6.30 | 17.3 | 3.50 | 1.71 | 3.00 | 0.0317 | 5.04 | 3890 |
| 59 | 6.40 | 17.7 | — | — | 3.10 | 0.0331 | 4.14 | 3950 |
| 60 | 6.20 | 17.7 | — | — | 3.00 | 0.0411 | 5.04 | 3490 |
| 61 | 6.30 | 17.5 | 3.43 | 2.79 | 3.00 | 0.0380 | 5.04 | 3790 |
| 62 | 6.10 | 17.5 | 3.46 | 2.16 | 3.00 | 0.0432 | 5.22 | 3540 |
| 63 | 6.10 | 17.6 | 3.50 | 2.70 | 3.00 | 0.0394 | 4.86 | 3900 |

As is illustrated in Table 4, the total acid content of Examples 49-63 was surprisingly higher than the total acid content of the other examples. In Examples 34-48, the total acid content after 1 month ranged from 2.70% to 4.50% with a mean value of 3.36%. In Examples 49-63, the total acid content after 1 month ranged from 4.14% to 5.40% with a mean value of 4.88%. Thus, cleaning the selected pineapples with a previously created fermented fruit solution rather than cleaning the selected pineapples with water results in superior cleaning compositions.

The present invention also provides for softening compositions comprising fermented fruit solutions and softening agents wherein the softening agents do not include quaternary ammonium compounds. The fermented fruit solutions help to dissolve impurities as a natural surfactant and act synergistically with the softening agents which are not quaternary ammonium compounds to soften articles. A significant number of tests were conducted to determine the capabilities of the present invention to soften an article. The softening compositions of the present invention have been shown both to soften fabrics on an absolute basis, and have been shown to soften fabrics better than (a) those brand names currently sold in Asia portraying themselves as 100% natural, which do not list in their ingredient list a quaternary ammonium compound and (b) white distilled vinegar, which is used in lieu of conventional fabric softeners by health and environment focused people.

In certain tests detailed below, softening compositions of the present invention were compared against (a) certain brand name natural fabric softeners which do not list in their ingredient mix quaternary ammonium compounds and (b) white distilled vinegar. Tests were also made comparing certain compositions with and without fermented fruit to show that adding fermented fruit with the softening agents of the present invention adds to the softening ability.

To determine the softening properties, tests were created to determine people's view of the primary function of the product, i.e., softening. That is, people were given fabrics which have been softened with the products of the present invention and asked to compare these products with other brand name products and/or vinegar (without knowing which fabrics were softened with which product) and were asked to rate the softening. Although such tests are inherently subjective, this is the method commonly and regularly used in the industry. In addition to the softening properties, a reduction of static electricity was measured. The reduction of static electricity was measured objectively through an electrostatic meter by measuring IB values. The lower the absolute value, i.e., the closer to zero, the better the reduction of static electricity (for this measurement, a SIMCO FMX-003 Electrostatic Fieldmeter was used).

In the experiments, the results of which are summarized in Tables 5-9, the following study methodology was used. For each softener test, cotton towels (each white 100% cotton with size of 75 cm×145 cm) were used. For test subjects to better distinguish fabric softeners, the fabric was roughened in the following way: each towel was washed with Haiter Color (35 ml) 10 times at the following settings: ambient temperature, spin cycle of 850. After the 10 times wash, the towels were dried (90 minutes cycle). The washers and dryers used were both Electrolux brands. Then, a second wash was performed with Haiter (35 ml) as laundry detergent and each respective fabric softener (20 ml) at a setting of ambient temperature (cotton setting on cold), spin cycle of 500. Test subjects were not told which brand of which fabric softener was used on which towel, and towels were coded with letters. Each experiment test subject was asked to rate the softening feeling (the higher the number the better).

For the experiment summarized in Table 5, for each towel, test subjects were asked to write down a number representing the softening feeling: "4" for best softening feeling, a "3" for next best, a "2" for 3$^{rd}$ best, and a "1" for worst feeling. The additions of the numbers added together from the test subjects create a softening value; the higher the value the better.

Table 5 (with Example 64 and Example 65) shows that fermented fruit works synergistically with the softening agents (which do not include quaternary ammonium compounds). For example, the only differences in formulation between Example 64 and Example 65 below is that Example 64 contains fermented fluid and Example 65 does not contain fermented fluid.

EXAMPLE 64

| Ingredient | % in solution |
|---|---|
| Fermented fruit | 15.7% |
| Guar gum | 0.3% |
| Gum Arabic | 0.2% |
| Polysorbate 80 | 0.1% |
| Lactic acid | 0.3% |
| Sodium acetate | 0.3% |
| Citric acid | 0.6% |
| Water | 78.3% |
| Calcium Chloride | 0.6% |
| Polyaspartate | 0.5% |

EXAMPLE 64

| Ingredient | % in solution |
|---|---|
| Boric acid | 2.0% |
| Glycerin | 0.9% |
| Potassium sorbate | 0.1% |
| Total | 100.0% |

EXAMPLE 65

| Ingredient | % in solution |
|---|---|
| Fermented fruit | 0.0% |
| Guar gum | 0.3% |
| Gum Arabic | 0.2% |
| Polysorbate 80 | 0.1% |
| Lactic acid | 0.3% |
| Sodium acetate | 0.3% |
| Citric acid | 0.6% |
| Water | 94.0% |
| Calcium Chloride | 0.6% |
| Polyaspartate | 0.5% |
| Boric acid | 2.0% |
| Glycerin | 0.9% |
| Potassium sorbate | 0.1% |
| Total | 100.0% |

TABLE 5

| Softening Composition | Softening Value |
|---|---|
| Example 64 | 11 |
| Example 65 | 7 |

Exemplary embodiments of the present invention used in experiments include Example 66, Example 67, Example 68, Example 69, Example 70, Example 71, Example 72 and Example 73. These exemplary embodiments are set forth below.

Example 66

| Ingredient | % in solution |
|---|---|
| Fermented Fruit | 15.7% |
| Guar gum | 0.3% |
| Gum Arabic | 0.2% |
| Polysorbate 80 | 0.1% |
| Lactic acid | 0.3% |
| Sodium acetate | 0.3% |
| Citric acid | 0.6% |
| Water | 73.3% |
| Calcium Chloride | 0.6% |
| Polyaspartate | 0.5% |
| Boric acid | 2.0% |
| Glycerin | 3.0% |
| Oleic acid | 3.0% |
| Potassium sorbate | 0.1% |
| Total | 100.0% |

Example 67

| Ingredient | % in solution |
|---|---|
| Fermented Fruit | 30.0% |
| Guar gum | 0.3% |
| Gum Arabic | 0.2% |
| Polysorbate 80 | 0.1% |
| Lactic acid | 0.3% |
| Sodium acetate | 0.3% |
| Citric acid | 0.6% |
| Water | 58.9% |
| Calcium Chloride | 0.6% |
| Polyaspartate | 0.5% |
| Boric acid | 2.0% |
| Glycerin | 3.0% |
| Oleic acid | 3.0% |
| Potassium sorbate | 0.1% |
| Total | 100.0% |

Example 68

| Ingredient | % in solution |
|---|---|
| Fermented fruit | 15.4% |
| Xanthan gum | 0.2% |
| Gum Arabic | 0.3% |
| Polysorbate 80 | 0.1% |
| Lactic acid | 0.3% |
| Sodium acetate | 0.3% |
| Citric acid | 0.6% |
| Water | 77.1% |
| Calcium Chloride | 0.6% |
| Polyaspartate | 0.5% |
| Boric acid | 2.0% |
| Glycerin | 0.9% |
| Oleic Acid | 1.5% |
| Potassium sorbate | 0.1% |
| Total | 100.0% |

Example 69

| Ingredient | % in solution |
|---|---|
| Water | 54.6 |
| Solec 8160 | 1.5 |
| Xanthan gum | 0.2 |
| Oleic acid | 2.5 |
| Vitamin E | 0.2 |
| Croduret 60-SO-(SG) | 2.5 |
| Scent | 0.3 |
| Glycerin | 5.0 |
| Fermented Fruit | 30.0 |

Example 69

| Ingredient | % in solution |
| --- | --- |
| Sodium Polyaspartate | 0.5 |
| Citric acid | 2.5 |
| Potassium sorbate | 0.2 |
| Total | 100.0 |

Example 70

| Ingredient | % in solution |
| --- | --- |
| Water | 57.7 |
| Solec 8160 | 1.5 |
| Oleic acid | 2.5 |
| Polysorbate 80 | 2.0 |
| Scent | 0.3 |
| Glycerin | 5.0 |
| Fermented Fruit | 30.0 |
| Sodium Polyaspartate | 0.5 |
| Lactic acid | 0.3 |
| Potassium sorbate | 0.2 |
| Total | 100.0 |

Example 71

| Ingredient | % in solution |
| --- | --- |
| Fermented Fruit | 30.0% |
| Guar gum | 0.3% |
| Gum Arabic | 0.2% |
| Polysorbate 80 | 2.0% |
| Lactic acid | 0.3% |
| Sodium acetate | 0.3% |
| Water | 58.3% |
| Calcium Chloride | 1.0% |
| Polyaspartate | 0.5% |
| Glycerin | 4.0% |
| Oleic acid | 3.0% |
| Potassium sorbate | 0.1% |
| Total | 100.0% |

Example 72

| Ingredient | % in solution |
| --- | --- |
| Fermented Fruit | 15.7% |
| Guar gum | 0.3% |
| Gum Arabic | 0.2% |
| Polysorbate 80 | 0.1% |
| Lactic acid | 0.3% |
| Sodium acetate | 0.3% |
| Citric acid | 0.6% |
| Water | 74.8% |
| Calcium Chloride | 0.6% |
| Polyaspartate | 0.5% |
| Boric acid | 2.0% |
| Glycerin | 3.0% |
| Oleic acid | 1.5% |
| Potassium sorbate | 0.1% |
| Total | 100.0% |

Example 73

| Ingredient | % in solution |
| --- | --- |
| Fermented Fruit | 15.7% |
| Guar gum | 0.3% |
| Gum arabic | 0.2% |
| Polysorbate 80 | 0.1% |
| Lactic acid | 0.3% |
| Sodium acetate | 0.3% |
| Citric acid | 0.6% |
| Water | 72.8% |
| Calcium Chloride | 0.6% |
| Polyaspartate | 0.5% |
| Boric acid | 2.0% |
| Glycerin | 5.0% |
| Oleic acid | 1.5% |
| Potassium sorbate | 0.1% |
| Total | 100.0% |

Table 6 illustrates another experiment showing fermented fluid improves softening ability. For the experiment summarized in Table 6, for each towel, test subjects were asked to write down a number representing the softening feeling: "2" for best softening feeling and a "1" for worse feeling. The additions of the numbers added together from the test subjects create a softening value; the higher the value, the better.

Table 6 shows that fermented fruit works synergistically with the softening agents (which do not include quaternary ammonium compounds). The only differences in formulation between Example 66 and Example 67 is that Example 66 contains fermented fluid at 16% and Example 67 contains fermented fluid at 30%. Example 66 and Example 67 are exemplary embodiments of the present invention.

TABLE 6

| Softening Composition | Softening Value |
| --- | --- |
| Example 66 | 12 |
| Example 67 | 18 |

In the 2 below experiments, summarized in Tables 7 and 8, for each towel, test subjects were asked to write down a number representing the softening feeling: "4" for best softening feeling, a "3" for next best, a "2" for $3^{rd}$ best, and a "1" for worst feeling. The additions of the numbers added together from the test subjects create a softening value; the higher the value the better. In Table 7, an exemplary embodiment of the present invention (Example 68) is compared against not using any fabric softener. In a separate experiment with a larger number of test subjects, an exemplary embodiment of the present invention (Example 68) is compared against fabric softener (FS) Brand A. As can be seen from Tables 7 and 8, Example 68 softens on an absolute basis versus no fabric softener and softens comparably to FS Brand A.

TABLE 7

| Softening Composition | Softening Value |
|---|---|
| Example 68 | 20 |
| No fabric softener | 11 |

As is illustrated by the above table, the softening composition of the present invention produced softening results on an absolute basis.

TABLE 8

| Softening Composition | Softening Value |
|---|---|
| Example 68 | 25 |
| FS Brand A | 26 |

As is illustrated by the above table, softening compositions of the present invention produced softening results that are comparable to brand name fabric softeners.

In the below experiment, summarized in Table 9, for each towel, test subjects were asked to write down a number representing the softening feeling: "2" for best softening feeling and a "1" for worse feeling. The additions of the numbers added together from the test subjects create a softening value; the higher the value the better. In addition, test subjects were asked to write down whether the towel felt "too stiff" or not (here the lowest, i.e., 0, would be best). In Table 9, an exemplary embodiment of the present invention (Example 69) is compared against each of FS Brand A, FS Brand B and white distilled vinegar.

TABLE 9

| Softening Composition | Softening Value | Too Stiff |
|---|---|---|
| Example 69 | 22 | 1 |
| FS Brand A | 12 | 10 |
| FS Brand B | 16 | 3 |
| white distilled vinegar | 12 | 3 |

As is illustrated by the above table, softening compositions of the present invention produced softening results which are better than brand name fabric softeners and also better than white distilled vinegar.

In Table 10, the fabrics were not roughened with Haiter as described above, and instead new towels were used; otherwise, the study methodology is the same as described above. As in the experiment summarized in Table 9, for each towel, test subjects were asked to write down a number representing the softening feeling: "2" for best softening feeling and a "1" for worse feeling. The additions of the numbers added together from the test subjects create a softening value; the higher the value, the better. In addition, test subjects were asked to write down whether the towel felt "too stiff" or not (here the lowest, i.e., 0, would be best). In Table 10, an exemplary embodiment of the present invention (Example 69) is compared against each of FS Brand A and FS Brand B.

TABLE 10

| Softening Composition | Softening Value | Too Stiff |
|---|---|---|
| Example 69 | 23 | 1 |
| FS Brand A | 13 | 9 |
| FS Brand B | 17 | 2 |

As is illustrated by the above table, softening compositions of the present invention produced softening results which are better than brand name fabric softeners.

In the below experiment, summarized in Table 11, the IB absolute values of an exemplary embodiment of the present invention (Example 69) is compared against each of FS Brand A and FS Brand B (the lower the absolute value, i.e., the closer to 0, the better).

TABLE 11

| | Example 69 | FS Brand A | FS Brand B |
|---|---|---|---|
| IB absolute value average | 106 | 125 | 130 |

As is illustrated by the above table, softening compositions of the present invention produced static electricity results which are better than brand name fabric softeners.

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the methods described above and illustrated in the drawings are shown as a sequence of steps, this was done solely for the sake of illustration. Accordingly, it is contemplated that some steps may be added, some steps may be omitted, the order of steps may be re-arranged, and some steps may be performed in parallel.

What is claimed is:

1. A method of making a softening composition comprising:
   preparing a pre-fermented fruit solution with a brix level of about 12% to about 24%, the pre-fermented fruit solution comprising:
   (i) about 2 to about 20 weight percent of a sugar based on the total weight of the pre-fermented fruit solution;
   (ii) about 20 to about 50 weight percent of a fruit puree based on the total weight of the pre-fermented fruit solution, wherein the fruit is more than 90% pineapple;
   (iii) about 30 to about 75 weight percent of a water based on the total weight of the pre-fermented fruit solution,
   fermenting the pre-fermented fruit solution with lactic acid bacteria to create a fermented fruit solution with a total acid content of greater than or equal to 2.0%; and
   mixing the fermented fruit solution with soy lecithin, oleic acid, glycerol, or a combination thereof in an amount of about 2 to about 18 weight percent based on the total weight of the composition.

2. The method of claim 1, wherein the soy lecithin, oleic acid, glycerol, or a combination thereof consists of soy lecithin and glycerol.

3. The method of claim 1, wherein the total weight percent of soy lecithin, oleic acid, glycerol, or a combination thereof is about 3 to about 12.5 weight percent based on the total weight of the composition.

4. The method of claim 1, wherein the total weight percent of soy lecithin, oleic acid, glycerol, or a combination thereof is about 5.5 to about 10 weight percent based on the total weight of the composition.

5. The method of claim 1, wherein the soy lecithin, oleic acid, glycerol, or a combination thereof consists of soy lecithin in an amount of about 1 to about 3 weight percent based on the total weight of the composition, oleic acid in an amount of about 1 to about 5 weight percent based on the total weight of the composition, and glycerol in an amount of about 1 to about 10 weight percent based on the total weight of the composition.

6. The method of claim 1, wherein the soy lecithin, oleic acid, glycerol, or a combination thereof consists of soy lecithin in an amount of about 1 to about 2.5 weight percent based on the total weight of the composition and glycerol in an amount of about 1 to about 7 weight percent based on the total weight of the composition.

7. The method of claim 1, wherein the soy lecithin, oleic acid, glycerol, or a combination thereof consists of soy lecithin in an amount of about 1.5 to about 2 weight percent based on the total weight of the composition and glycerol in an amount of about 2 to about 5 weight percent based on the total weight of the composition.

8. A method of making a softening composition comprising:
preparing a pre-fermented fruit solution with a brix level of about 12% to about 24%, the pre-fermented fruit solution comprising:
(i) about 2 to about 20 weight percent of a sugar based on the total weight of the pre-fermented fruit solution;
(ii) about 20 to about 50 weight percent of a fruit puree based on the total weight of the pre-fermented fruit solution, wherein the fruit is more than 90% pineapple;
(iii) about 30 to about 75 weight percent of a water based on the total weight of the pre-fermented fruit solution,
fermenting the pre-fermented fruit solution with lactic acid bacteria to create a fermented fruit solution with a total acid content of greater than or equal to 2.0%;
mixing the fermented fruit solution with soy lecithin, oleic acid, glycerol, or a combination thereof in an amount of about 2 to about 18 weight percent based on the total weight of the composition;
adding at least one antioxidant;
adding at least one emulsifier;
adding at least one pH adjusting agent; and
adding a mixture of at least one thickener.

9. The method of claim 8, wherein the soy lecithin, oleic acid, glycerol, or a combination thereof consists soy lecithin and glycerol.

10. The method of claim 8, wherein the total weight percent of soy lecithin, oleic acid, glycerol, or a combination thereof is about 3 to about 12.5 weight percent based on the total weight of the composition.

11. The method of claim 8, wherein the total weight percent of soy lecithin, oleic acid, glycerol, or a combination thereof is about 5.5 to about 10 weight percent based on the total weight of the composition.

12. The method of claim 8, wherein the soy lecithin, oleic acid, glycerol, or a combination thereof consists of soy lecithin in an amount of about 1 to about 3 weight percent based on the total weight of the composition and glycerol in an amount of about 1 to about 10 weight percent based on the total weight of the composition.

13. The method of claim 8, wherein the soy lecithin, oleic acid, glycerol, or a combination thereof consists of soy lecithin in an amount of about 1 to about 2.5 weight percent based on the total weight of the composition and glycerol in an amount of about 1 to about 7 weight percent based on the total weight of the composition.

14. The method of claim 8, wherein the soy lecithin, oleic acid, glycerol, or a combination thereof consists of soy lecithin in an amount of about 1.5 to about 2 weight percent based on the total weight of the composition and glycerol in an amount of about 2 to about 5 weight percent based on the total weight of the composition.

15. The method of claim 8, wherein the at least one antioxidant agent is used in an amount of about 0.2 to about 1 weight percent based on the total weight of the composition.

16. The method of claim 8, wherein the antioxidant agent is vitamin E.

17. The method of claim 8, wherein the at least one emulsifier is used in an amount of about 2 to about 5 weight percent based on the total weight of the composition.

18. The method of claim 8, wherein the at least one emulsifier is selected from the group consisting of PEG-60 hydrogenated castor oil, polyoxyethylene (20) sorbitan monooleate, sorbitan monooleate, and mixtures thereof.

19. The method of claim 8, wherein the at least one pH adjusting agent is selected from the group consisting of citric acid, lactic acid, and mixtures thereof.

20. The method of claim 8, wherein the at least one pH adjusting agent is used in an amount of about 2 to about 5 weight percent based on the total weight of the composition.

21. The method of claim 8, wherein the at least one thickener is used in an amount of about 0.1 to about 2 weight percent based on the total weight of the composition.

22. The method of claim 8, wherein the at least one thickener is selected from the group consisting of sodium chloride, and natural gums selected from the group consisting of guar gum, xanthan gum and gum arabic, and mixtures thereof.

23. The method of claim 8 further comprising: adding at least one preservative.

24. The method of claim 23, wherein the preservative is selected from the group consisting of boric acid, benzoic acid, potassium sorbate, nisin, natamycin and mixtures thereof, and, if the preservative is boric acid it is used in an amount not greater than about 2 weight percent based on the total weight of the composition, and if the preservative is not boric acid, it is used in an amount not greater than about 1 weight percent based on the total weight of the composition.

25. The method of claims claim 23, wherein the preservative is selected from the group consisting of potassium sorbate, nisin, natamycin and mixtures thereof, and is used in an amount not greater than about 1 weight percent based on the total weight of the composition.

26. The method of claim 8, further comprising: adding at least one corrosion inhibitor.

27. The method of claim 26, wherein the at least one corrosion inhibitor is used in an amount of about 0.1 to about 2.5 weight percent based on the total weight of the composition.

28. The method of claim 27, wherein the at least one corrosion inhibitor is selected from the group consisting of gum arabic, sodium polyaspartate and mixtures thereof.

29. The method of claim 8 further comprising:
adding at least one selected from the group consisting of an essential oil and a fragrance.

* * * * *